United States Patent [19]

Vickers

[11] Patent Number: 5,140,998
[45] Date of Patent: Aug. 25, 1992

[54] SURGICAL HAND RESTRAINER

[76] Inventor: David W. Vickers, 225 Wickham Ter., Brisbane, State of Queensland, 4000, Australia

[21] Appl. No.: 692,168

[22] Filed: Apr. 26, 1991

[30] Foreign Application Priority Data

Jul. 11, 1990 [AU] Australia ............... PK1117

[51] Int. Cl.⁵ ............... A61F 5/37; A61G 13/00
[52] U.S. Cl. ................... 128/879; 128/880; 128/878; 602/21; 602/22; 5/621
[58] Field of Search .............. 128/877–880, 128/77; 269/328; 434/296–297; 40/586; 119/96, 103

[56] References Cited

U.S. PATENT DOCUMENTS

| Re. 24,377 | 10/1957 | Creelman | 269/328 |
|---|---|---|---|
| 3,198,197 | 8/1965 | Van Halanger | 128/77 X |
| 3,286,694 | 11/1966 | Landy | 269/328 X |
| 3,318,597 | 5/1967 | Briggs | 269/328 |
| 3,484,096 | 12/1969 | Briggs | 269/328 |
| 3,746,332 | 7/1973 | Hakstian | 269/328 |
| 3,762,401 | 10/1973 | Tupper | 128/879 X |
| 3,818,905 | 6/1974 | Lebold | 128/77 |
| 3,971,950 | 7/1976 | Evans et al. | 269/328 X |
| 3,976,066 | 8/1976 | McCartney | 128/879 X |
| 4,082,257 | 4/1978 | Strickland | 269/328 |
| 4,204,533 | 5/1980 | Forster et al. | 269/328 X |
| 4,220,334 | 9/1980 | Kanamoto et al. | 128/77 X |
| 4,456,002 | 6/1984 | Barber et al. | 128/77 |
| 4,674,110 | 6/1987 | Eaton et al. | 128/77 X |
| 4,781,178 | 11/1988 | Gordon | 128/77 |
| 4,840,168 | 6/1989 | Lonardo | 128/77 |
| 4,982,744 | 1/1991 | Stanec | 128/879 X |

Primary Examiner—Richard J. Apley
Assistant Examiner—Linda C. M. Dvorak
Attorney, Agent, or Firm—Iandiorio & Dingman

[57] ABSTRACT

A surgical hand restrainer including a plate for supporting the hand, a clamping member for restraining the fingers in a fixed position on the support plate, and a restraining device for retaining the thumb on the support plate.

11 Claims, 2 Drawing Sheets

SURGICAL HAND RESTRAINER

This invention relates to a surgical hand restrainer suitable for restraining the hand of fingers during a surgical operation.

Surgical hand restrainers have been previously described in the patent literature. U.S. Pat. No. 3,762,401 for example refers to a shaped pallet with notches located about its periphery on which the and is placed wound side up. There are provided elastic finger bands for holding the fingers in place on the pallet which are located in slots or cut outs located in the pallet adjacent each finger. There is also provided one or more flexible ball and link chains with a hook at one end which is hooked over the edge of the wound and which is fastened to the pallet edge or periphery at a predetermined point along its length by inserted one of the links into one of the pallet notches to hold the wound open.

Reference also may be made to U.S. Pat. No. 4,204,533 which also describes a surgical hand restrainer comprising a plate which is configured as a hand with spread apart fingers and elastic removable rings positioned over some of the fingers of the patient and the fingers of the plate to secure the hand to the plate.

Other prior art of interest includes U.S. Pat. No. 3,581,740 which describes an inflatable splint for extending the fingers and wrist of the hand of the wearer. The splint has an inflatable chamber extending over the hand and wrist area of the wearer with one surface which assumes a planar configuration when the splint is inflated. This planar surface has finger loops adapted to receive the fingers of the wearer and the finger loops are positioned such that upon inflation the fingers will be moved to a normally extend spaced apart position.

U.S. Pat. No. 3,198,197 also describes a manicure nail protector with detachable finger partitions which may be used to support a hand during a manicure.

Australian Patent Specification 76110/81 also describes a surgical table for hand surgery comprising arm supporting elements and finger supporting elements the latter of which comprise flexible arms at the end of which resilient thimbles and/or instrument holding elements are provided.

There is also know a device known as a "a lead hand" comprising a hand template formed from lead which held the fingers by folding back the finger portions to restrain the fingers in position.

There was also known a hand support known as a ROTALOC device having a plurality of perforations which functioned by placing a number of disposable finger supports in each perforation and each finger was supported by one or more of the finger supports with rubber bands being used to restrain the hand in the desired position. The finger supports included a male projection for engaging a respective female perforation or socket. The ROTALOC device was also attached to a tiltable support with a locking handle.

The aforementioned prior art had a number of significant disadvantages. Thus for example the perforated plate described above was expensive to manufacture and time consuming in operation with it being necessary to place each finger support in a corresponding perforation and fasten the fingers by rubber bands. The perforated plate also had to be autoclaved after each operation and was slow to cool being formed from thick synthetic material.

The "lead hand" described above was easily fractured and was also toxic. It was also slow cooling after autoclaving.

The use of finger bands or finger loops and also rubber bands generally was found to be time consuming. Use of flexible ball link chains as described in U.S. Pat. No. 3,762,401 were also found to be unduly expensive and time consuming in application.

Another deficiency of the abovementioned prior art was the necessity to provide the hand restrainer when used as a hand template having the shape of a human hand to supply the template in both a left handed and right handed configuration.

It therefore is an object of the invention to provide a hand surgical restrainer which may alleviate the disadvantages of the prior art described above.

The hand restrainer of the invention includes a support plate, a clamping member for restraining a plurality of fingers in a fixed position on the support plate, and thumb retaining means for retention of a thumb on the support plate.

The thumb retaining means may comprise two separate thumb retaining members which are provided on a common support plate or more suitably a single thumb retaining member which is attached to the support plate so as to retain either a left handed thumb or a right handed thumb. This may necessitate the provision of a support plate suitable for a left hand and another support plate suitable for a right hand. To overcome this problem it is preferable to have a single thumb retaining member attached to the support plate and movable thereto so as to accommodate a right handed thumb or a left handed thumb.

Preferably there is also provided biassing means for biassing the clamping member to the fixed position.

The support plate may have any suitable shape such as round, elliptical, rectangular or polygonal. Suitably the support plate has two separate regions a narrow region which supports the clamping member and a broader region which supports the thumb retaining member.

The support plate may also be provided with a plurality of notches located in a peripheral edge thereof. The notches may be provided for the purpose of using elastic bands or rubber bands which may be utilised as an auxiliary hand restrainer or finger restrainer if such as considered appropriate. The notches may also be utilised for retention of the rubber bands on the support plate when the hand restrainer of the invention is not in use.

The clamping member may comprise a clamping rod or clamping bar which is attached to the support plate in any appropriate manner. Suitably there are provided a pair of spaced attachment brackets having a support surface and opposed ends each of which have aligned apertures for retaining an associated end portion of the clamping rod.

Preferably the clamping rod or bar has end portions which are U shaped or V shaped although this is not necessary and the clamping rod may comprise a substantially straight rod if desired attached to the support plate at each end.

The clamping rod may also have any desired shape such as arcuate but is preferably part rectangular having the aforementioned U shaped ends and a body part intermediate the U shaped ends.

The biassing means associated with the clamping member may be of any suitable type and thus comprises a single spring, a torsion member or more preferably a pair of springs associated with each end of the clamping member. The biassing means is such that it urges the clamping member toward the desired fixed position or restraining position of the hand and thus suitably the clamping member is urged downwardly towards the support plate.

In a preferred embodiment of the invention there may be provided a pair of torsion springs with each spring fixed at one end and the other end being movable with each torsion spring surrounding an adjacent part of the clamping rod. Suitably each torsion spring is interposed between the ends of each attachment bracket.

There also may be provided one or more preferably a pair of cut outs or apertures in the support plate adjacent each end of the clamping member to facilitate elevation of the clamping member when desired. In this regard each cut out or aperture may provided access to a finger or thumb to elevate the clamping member.

The thumb retaining member is suitably in the form of a continuous loop of any suitable shape such as round or rectangular although this is not strictly necessary and each thumb retaining loop may be of a partly closed or arcuate configuration if desired.

The thumb retaining member may be movable relative to the support plate and suitable means may be provided for this purpose such as one or more preferably a pair of elongate slots being located in the support plate where each elongate slot may support an associated part such as an end or side of the thumb retaining member. This means enables the thumb retaining member to be freely movable in the support slots from one end of each slot to the other end of each slot so as to provide a right handed or left handed orientation as desired. This also provides a further advantage in providing a facility for catering for hands of different sizes.

Reference may now be made to a preferred embodiment of the present invention as illustrated in the attached drawings wherein.

Figure 2:
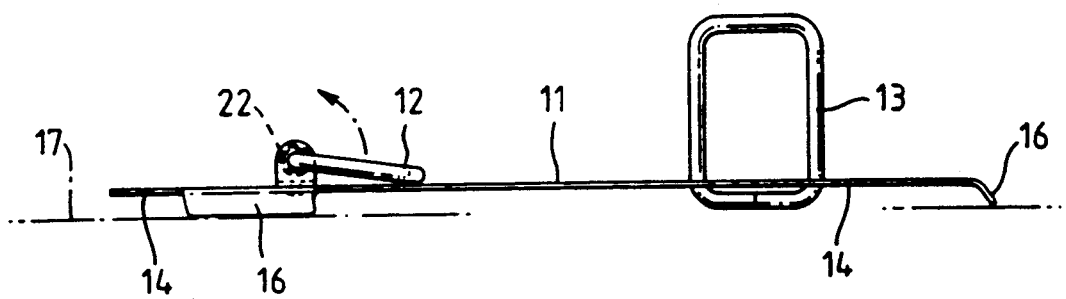
FIG. 2 is a side view of the hand restrainer shown in FIG. 1.

In the drawings there is shown hand restrainer 10 including support plate 11, clamping rod 12 and thumb remaining loop 13. There is also shown notches 14 located in a peripheral edge 15 of the support plate 11 as well as feet or downturned flanges 16 for elevating the plane of support plate 11 above a planar support surface 17 shown in phantom in FIG. 2. The thumb retaining loop 13 is supported in a pair of spaced arcuate slots 18 so as to make the loop 13 freely movable from one side of the support plate 11 to the other.

Figure 1:
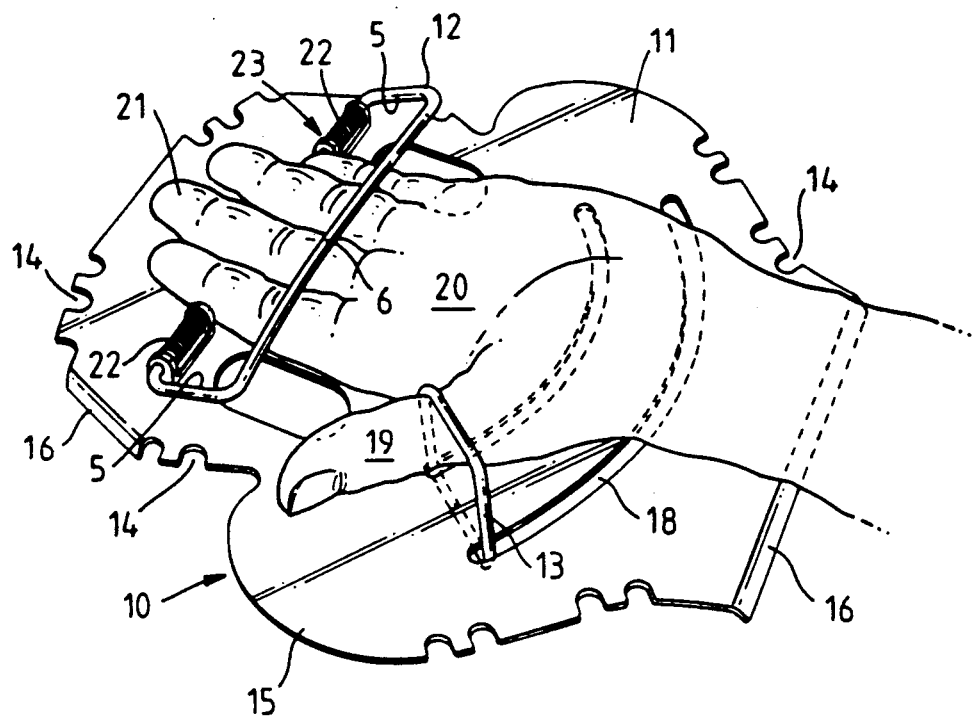
FIG. 1 is a perspective view of a hand restrainer constructed in accordance with the invention.
Figure 3:
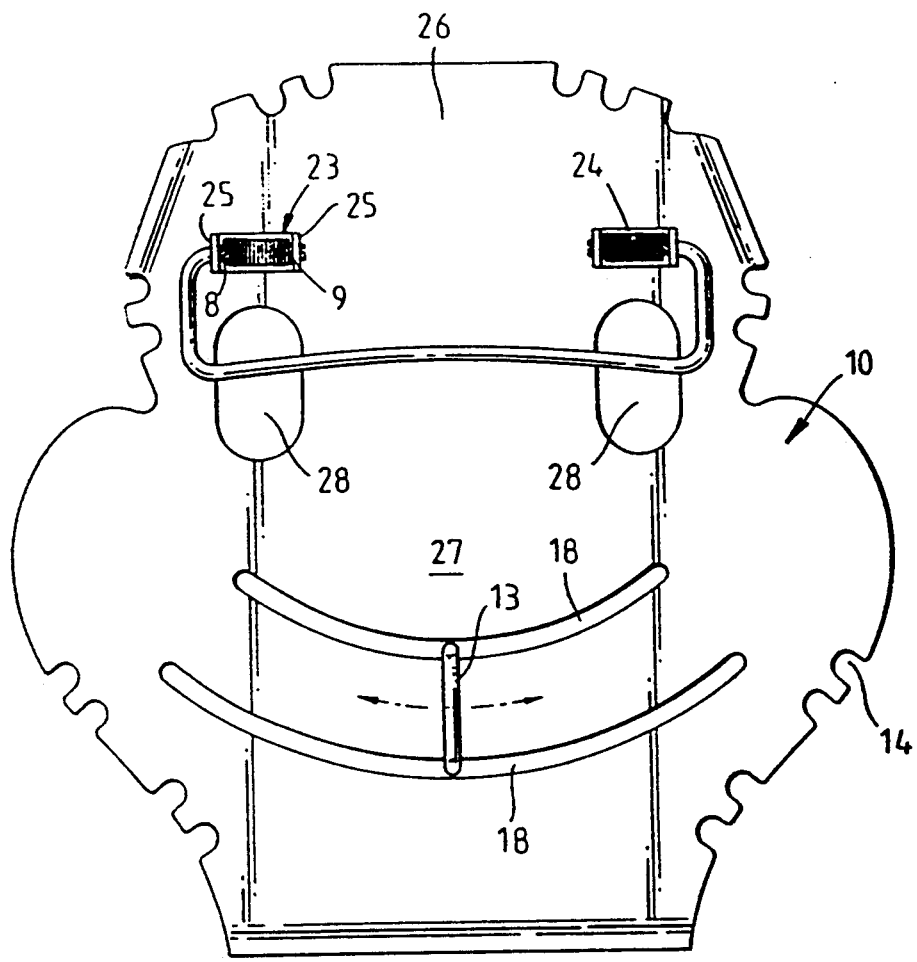
FIG. 3 is a plan view of the hand restrainer shown in FIG. 1.
Figure 4:
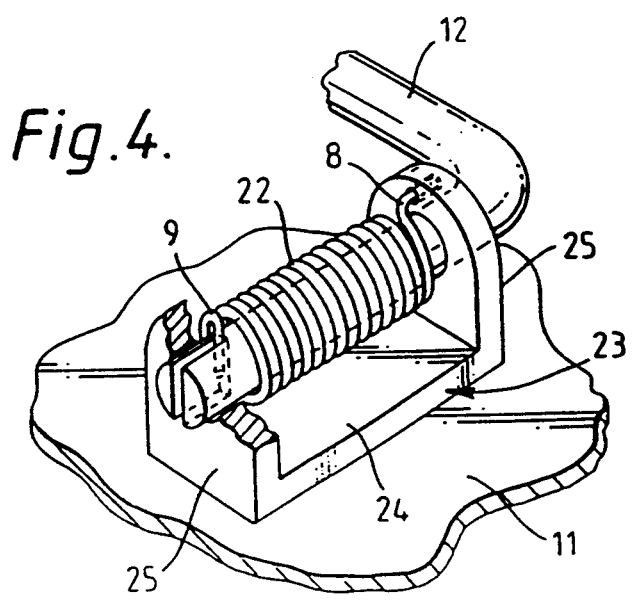
FIG. 4 is a detailed view of the engagement of each torsion spring with an associated clamping member attachment bracket.

As shown specifically in FIG. 1 and FIG. 3 the loop. 13 is movable from a proximal position shown in FIG. 1 suitable for retaining a left handed thumb 19 of hand 20 to a distal position having regard to FIG. 1 which is suitable for supporting a right handed thumb. The fingers 21 of hand 20 are shown firmly restrained by clamping rod 12 which is biassed to the hand fixing position or downward position having regard to support plate 11. Clamping rod 12 has opposed U-shaped ends 5 and body part 6 located intermediate each U-shaped end 5 for engaging fingers 21. There is also provided torsion springs 22 which bias the clamping rod 12 to the downward position which as shown in FIG. 4 have one end fixed and the other end which is movable. In the illustrated embodiment each attachment bracket 23 comprises a support surface 24 and opposed ends 25. Each torsion spring 22 has an outer end 8 fixed to an adjacent end 25 and an inner end 9 which is attached to clamping rod 12 as shown so that spring 22 twists upon rotation of clamping rod 22. This provides a downward bias on clamping rod 12.

It will also be appreciated from the illustrated embodiment that not all fingers 21 of hand 20 need to retained by clamping rod 12.

Preferably the support plate 11 is formed from Aluminum so as to be quick cooling after autoclaving. The support plate 11 is also suitably arodised to avoid having a shiny or reflective surface in the harsh glare of operating theatre lights.

The support plate 11 is also divided into a relatively narrow region 26 which includes clamping rod 12 as well as a relatively broad region 27 which includes thumb retaining loop 13 and slots 18. In the narrow region 26 there is also provided access apertures 28 for enabling a finger or thumb to gain proper access for elevation of clamping rod 12 when desired.

The slots 18 are preferably arcuate as illustrated for provided variability in enabling the thumb retaining loop 13 to accommodate hands of varying sizes. The arcuate slots 18 also enable the thumb retaining loop 13 to be originated at an angle to a longitudinal axis of support plate 11 so as to accommodate thumb 19 which is oriented at a similar angle as shown in FIG. 1.

I claim:

1. A surgical hand restrainer including:
   a support plate;
   a clamping rod attached to the support plate at each end of the clamping rod;
   a spring surrounding each end of the clamping rod so as to bias the clamping rod to a fixed position wherein the clamping rod restrains a plurality of fingers on the support plate simultaneously in use; and
   thumb retaining means for retention of a thumb on the support plate.

2. A surgical hand restrainer as claimed in claim 1 wherein each spring has one end fixed and the other end movable to function as a torsion spring.

3. A surgical hand restrainer as claimed in claim 2, wherein there are provided attachment brackets for each end of the clamping rod and the fixed end of each spring is attached to a respective attachment bracket.

4. A surgical hand restrainer as claimed in claim 1 wherein the clamping rod has opposed U-shaped ends and a body part for engagement with the fingers located intermediate each U-shaped end.

5. A surgical hand restrainer as claimed in claim 1 wherein there is provided adjacent each end of the clamping rod an access aperture for elevation of the clamping rod when required.

6. A surgical hand restrainer as claimed in claim 1 wherein the thumb retaining means is a thumb retaining member freely movable on the support plate.

7. A surgical hand restrainer as claimed in claim 6, wherein the thumb retaining member is retained on the support plate by a pair of slots.

8. A surgical hand restrainer as claimed in claim 7, wherein each slot is arcuate.

9. A surgical hand restrainer as claimed in claim 7, wherein the thumb retaining member comprises a continuous loop with opposed parts of the loop retained in an associated slot.

10. A surgical hand restrainer including a support plate, a clamping member for restraining a plurality of fingers in a fixed portion on the support plate and a thumb retaining member freely movable on the support plate and retained in a desired position by a continuous loop engageable in a pair of slots on the support plate.

11. A surgical hand restrainer as claimed in claim 10, wherein each slot is arcuate.

* * * * *